(12) United States Patent
Ishino et al.

(10) Patent No.: US 9,080,262 B2
(45) Date of Patent: Jul. 14, 2015

(54) APPARATUS FOR BULKING NONWOVEN FABRIC

(75) Inventors: Yuichi Ishino, Utsunomiya (JP); Akio Morita, Ichikai-machi (JP)

(73) Assignee: KAO CORPORATION, Tokyo (JP)

( * ) Notice: Subject to any disclaimer, the term of this patent is extended or adjusted under 35 U.S.C. 154(b) by 285 days.

(21) Appl. No.: 13/814,253

(22) PCT Filed: Aug. 1, 2011

(86) PCT No.: PCT/JP2011/067611
§ 371 (c)(1),
(2), (4) Date: Mar. 22, 2013

(87) PCT Pub. No.: WO2012/017990
PCT Pub. Date: Feb. 9, 2012

(65) Prior Publication Data
US 2013/0174379 A1  Jul. 11, 2013

(30) Foreign Application Priority Data
Aug. 6, 2010 (JP) ................................. 2010-178197

(51) Int. Cl.
*D01G 15/12* (2006.01)
*A61F 13/15* (2006.01)
(Continued)

(52) U.S. Cl.
CPC .......... *D01G 15/12* (2013.01); *A61F 13/15707* (2013.01); *D04H 1/558* (2013.01); *D04H 1/559* (2013.01); *D04H 1/72* (2013.01); *D06B 5/08* (2013.01); *D06C 7/00* (2013.01)

(58) Field of Classification Search
CPC ......... D04H 1/72; D04H 1/558; D04H 1/559; D06C 7/00; D06B 5/08; D01G 15/12
USPC .................... 19/161.1, 296, 304, 308; 28/167
See application file for complete search history.

(56) References Cited

U.S. PATENT DOCUMENTS 4,592,708 A * 6/1986 Feist et al. ................... 425/80.1
4,712,277 A * 12/1987 Gustavsson ..................... 19/296
(Continued)

FOREIGN PATENT DOCUMENTS

CN  1497086 A  5/2004
JP  63-2791 U  1/1988
(Continued)

OTHER PUBLICATIONS

International Search Report issued in PCT/JP2011/067611, mailed on Sep. 13, 2011.
(Continued)

*Primary Examiner* — Shaun R Hurley
(74) *Attorney, Agent, or Firm* — Birch, Stewart, Kolasch & Birch, LLP (57) ABSTRACT

A bulking apparatus includes a hot air generator, an air supply duct having an inlet for receiving hot air and an outlet for delivering hot air to nonwoven fabric, and a sucking part sucking in hot air delivered from the outlet and passed through nonwoven fabric. The air supply duct has an inflow portion leading hot air introduced into the inlet to flow in parallel to the transverse direction of the nonwoven fabric and an outflow portion forming an angle with the inflow portion leading hot air flowing through the inflow portion to the outlet. The air supply duct has a plurality of baffle plates disposed therein, each baffle plate having a flow-facing part and a flow-guiding part located in the inflow and outflow portions, respectively. The baffle plates are arranged such that the inflow path in the inflow portion has a decreasing cross-sectional area with distance from the inlet.

13 Claims, 6 Drawing Sheets

(51) Int. Cl.
*D04H 1/72* (2012.01)
*D06C 7/00* (2006.01)
*D04H 1/558* (2012.01)
*D04H 1/559* (2012.01)
*D06B 5/08* (2006.01)

(56) References Cited

U.S. PATENT DOCUMENTS

| | | | |
|---|---|---|---|
| 4,764,325 A * | 8/1988 | Angstadt | 264/113 |
| 4,859,388 A * | 8/1989 | Peterson et al. | 264/121 |
| 4,908,175 A * | 3/1990 | Angstadt | 264/113 |
| 5,064,484 A * | 11/1991 | Craig et al. | 156/62.6 |
| 5,097,574 A * | 3/1992 | Hertel et al. | 28/105 |
| 7,832,061 B2 * | 11/2010 | Hergeth | 19/303 |
| 2004/0111848 A1 | 6/2004 | Miyamoto et al. | |
| 2004/0255430 A1 * | 12/2004 | Catry et al. | 19/296 |
| 2011/0061214 A1 * | 3/2011 | Wirtz et al. | 28/104 |
| 2011/0126388 A1 * | 6/2011 | Takabayashi et al. | 28/104 |
| 2011/0191994 A1 | 8/2011 | Takahashi | |

FOREIGN PATENT DOCUMENTS

| | | |
|---|---|---|
| JP | 5-35856 U | 5/1993 |
| JP | 9-243127 A | 9/1997 |
| JP | 2000-77843 A | 3/2000 |
| JP | 2008-231609 A | 10/2008 |
| JP | 2012-63060 A | 3/2012 |
| WO | WO 2010/047292 A1 | 4/2010 |

OTHER PUBLICATIONS

Written Opinion of the International Searching Authority issued in PCT/JP2011/067611, mailed on Sep. 13, 2011.

English translation of the Written Opinion of the International Searching Authority, dated Sep. 13, 2011, for International Application No. PCT/JP2011/067611.

International Preliminary Report on Patentability, dated Mar. 12, 2013, for International Application No. PCT/JP2011/067611.

* cited by examiner

Fig. 7

APPARATUS FOR BULKING NONWOVEN FABRIC

TECHNICAL FIELD

The present invention relates to an apparatus for bulking nonwoven fabric.

BACKGROUND ART

Nonwoven fabric as obtained is generally wound into roll form to be transported or stored and unrolled to be processed into a desired form for use as a material for producing disposable diapers, cleaning sheets, and the like. A sheet in roll form decreases in bulkiness due to great winding pressure. There has been proposed a method for restoring bulkiness of nonwoven fabric whose bulk has been reduced under winding pressure as disclosed in patent literature 1 (see below).

The assignee common to this patent application proposed in patent literature 1 a method for restoring bulkiness of nonwoven fabric which contains crimped the thermoplastic fiber and is in a roll form. The method includes unwinding the nonwoven fabric from a stock roll and blowing hot air at a temperature lower than the melting point of the thermoplastic fiber to the unwound nonwoven fabric to make the nonwoven fabric increase in bulkiness.

A hot air heating apparatus capable of controlling the heating temperature is proposed in patent literature 2 below, in which the temperature fluctuation of the hot air blown to a substrate is minimized.

Patent literature 2 discloses a system composed of hot air heating units. Each unit includes a casing having therein a fan for air circulation, a heater, tubular nozzles, and hot air guide plates. The tubular nozzle has therein equally spaced baffle plates so as to blow hot air from its slit uniformly onto a substrate.

CITATION LIST

Patent Literature

Patent literature 1: US 2004/111848A1
Patent literature 2: JP 2000-077843A

SUMMARY OF INVENTION

Technical Problem

Equipment for producing disposable diapers, cleaning sheets or like articles may include an apparatus for bulking nonwoven fabric at the end of the process. From the standpoint of space saving, such a bulking apparatus is required to be compact in size. The problem with a compact bulking apparatus is that it is incapable of applying hot air of a desired temperature in a desired amount to nonwoven fabric with good precision.

The present invention relates to an apparatus for bulking nonwoven fabric that is compact and yet achieves precisely controlling the temperature and the amount of hot air.

Solution to Problem

The invention provides an apparatus for bulking nonwoven fabric including a hot air generator, an air supply duct having an inlet for receiving hot air from the hot air generator and an outlet for delivering the hot air to a nonwoven fabric being transported, and a sucking part sucking in hot air delivered from the outlet to the nonwoven fabric and passed through the nonwoven fabric.

The air supply duct has an inflow portion that leads the hot air introduced into the inlet to flow in parallel to the transverse direction of the nonwoven fabric and an outflow portion that forms an angle with the inflow portion to lead the hot air having flowed through the inflow portion to the outlet.

The air supply duct has a plurality of baffle plates disposed therein, each baffle plate having a flow-facing part and a flow-guiding part located in the inflow portion and the outflow portion, respectively. The plurality of baffle plates are arranged such that the inflow path in the inflow portion has a decreasing cross-sectional area with distance from the inlet.

The invention also provides a method for bulking nonwoven fabric being transported by suction using hot air supplied from the outlet of an air supply duct and passed through the nonwoven fabric. The method includes introducing hot air generated in a hot air generator into an air supply duct through an inlet, advancing the hot air in the air supply duct in a direction parallel to the transverse direction of the nonwoven fabric, directing the hot air against a plurality of baffle plates arranged spacedly in the direction parallel to the transverse direction of the nonwoven fabric such that the flow of the hot air is diverted to the thickness direction of the nonwoven fabric while being branched into a plurality of paths separated from each other by the baffle plates, and delivering the hot air having flowed through the plurality of paths to the nonwoven fabric.

The invention also provides a method for making an absorbent article. The method is characterized by using a nonwoven fabric obtained by the above described method for bulking nonwoven fabric. The method includes superposing the nonwoven fabric on a sheet material, uniting the nonwoven fabric and the sheet material, and cutting the united nonwoven fabric and the sheet material into an individual absorbent article.

DESCRIPTION OF EMBODIMENTS

The invention will be described based on its preferred embodiments with reference to the accompanying drawings.

Figure 1:
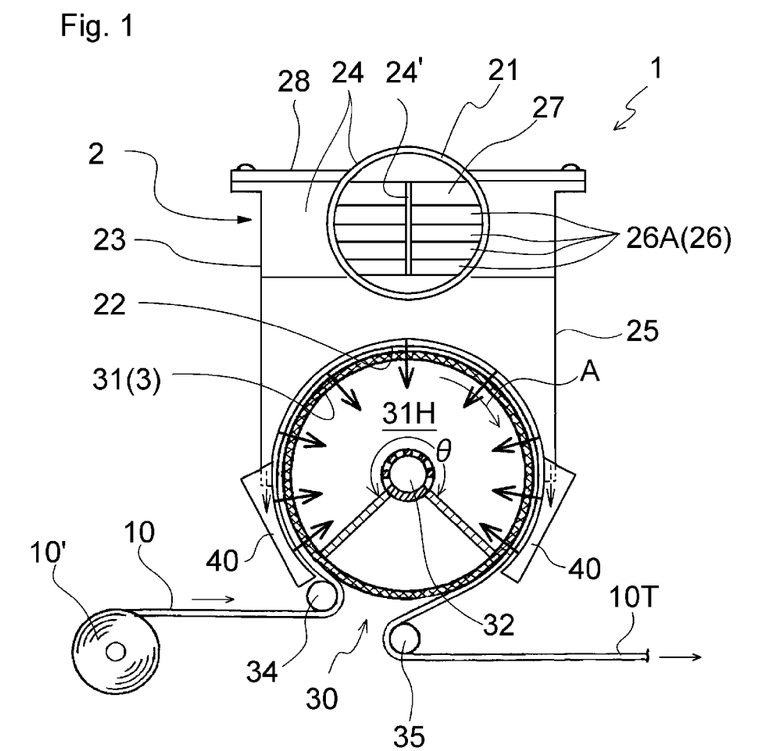
FIG. 1 is a schematic view of an embodiment of the apparatus and method for bulking nonwoven fabric according to the invention.

FIG. 1 schematically illustrates a first embodiment of the apparatus for bulking nonwoven fabric according to the invention. The first embodiment of the apparatus for bulking nonwoven fabric according to the invention will be described first.

Figure 2:
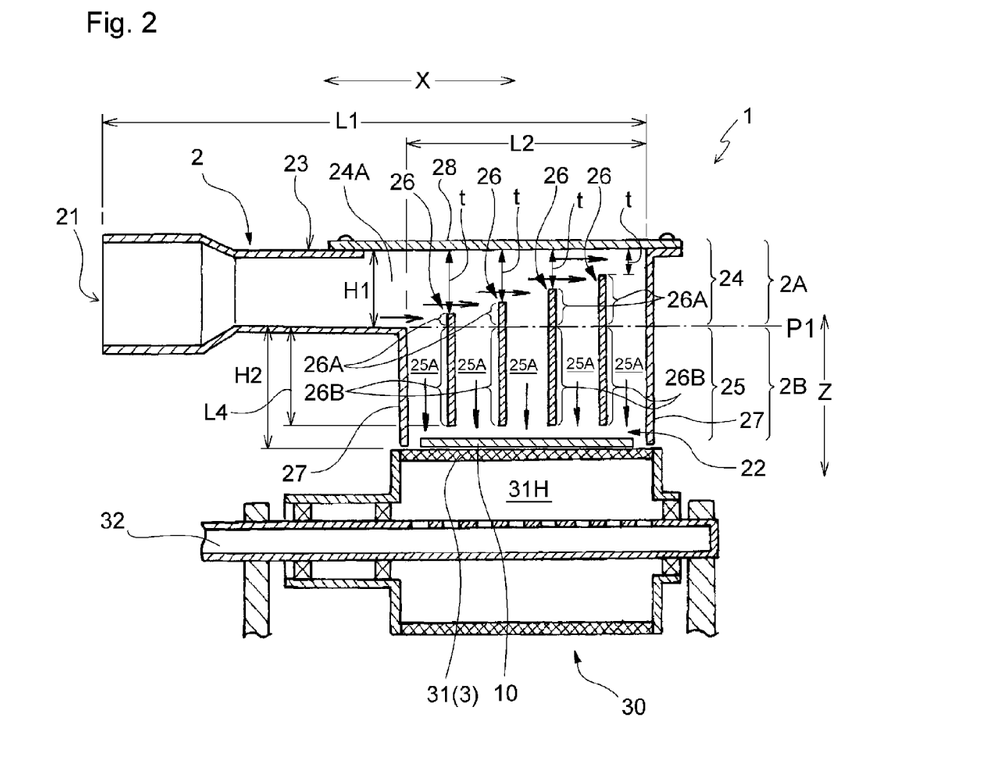
FIG. 2 is a schematic illustrating a cross-sectional structure of the bulking apparatus of FIG. 1.
Figure 3:
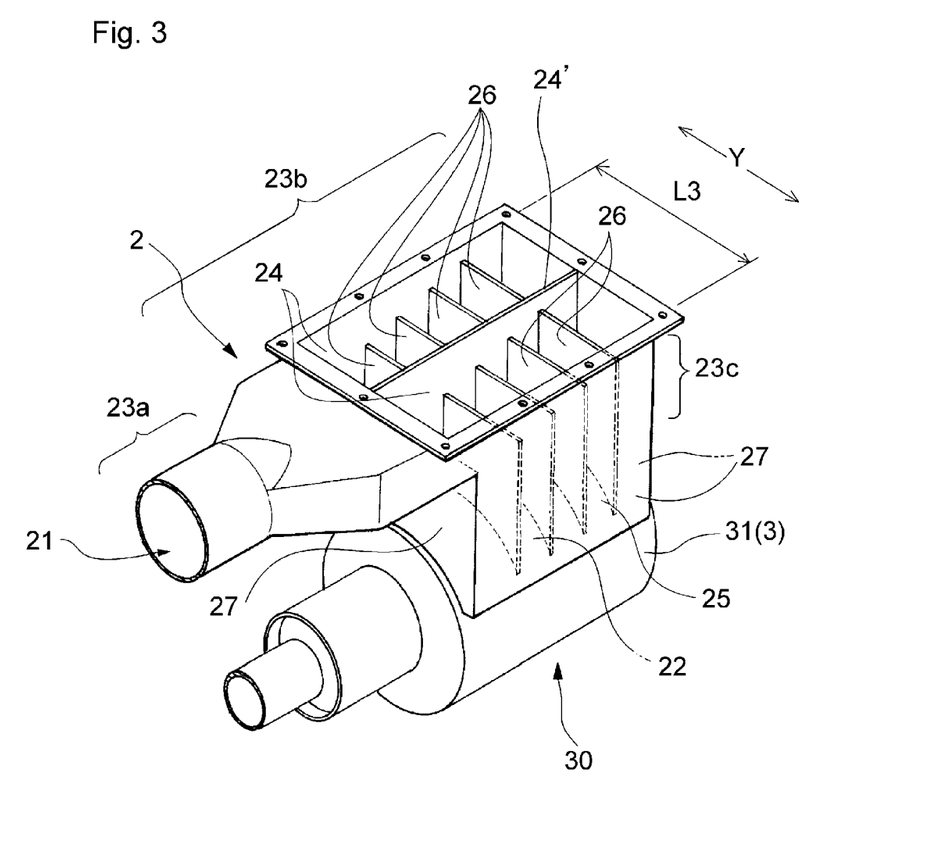
FIG. 3 is a perspective illustrating a part of the bulking apparatus of FIG. 1.

As shown in FIGS. 1 through 3, the bulking apparatus 1 includes an unshown hot air generator, an air supply duct 2 having an inlet 21 for receiving hot air supplied from the hot air generator and an outlet 22 for delivering the hot air to a nonwoven fabric 10, and a sucking part 3 sucking in the hot air having supplied from the outlet 22 to the nonwoven fabric 10 and passed through the nonwoven fabric 10. The hulking apparatus 1 is able to increase the bulk of the nonwoven fabric 10 being transported. The air supply duct 2 is constructed of a housing 23 that is closed except at the inlet 21 and the outlet 22.

The bulking apparatus 1 includes a rotary sucking unit 30. The rotary sucking unit 30 has a rotary drum 31 that sucks in air from its peripheral surface.

Specifically, the rotary sucking unit 30 includes a rotary drum 31 having an air permeable peripheral surface and an evacuating means 32 (part of which is shown) that evacuates the inside of the rotary drum 31. The rotary drum 31 corresponds to the sucking part 3 in the present embodiment.

As shown in FIG. 1, the rotary sucking unit 30 has a guiding-in means 34 that guides nonwoven fabric 10 unrolled from a stock roll 10' and transported up to a prescribed position of the bulking apparatus 1 onto the peripheral surface of the rotary drum 31, and a guiding-out means 35 that separates the nonwoven fabric 10 having been transported over a prescribed distance as wrapped around the peripheral surface of the rotary drum 31 from the peripheral surface of the rotary drum 31 and delivers the separated nonwoven fabric 10 to a subsequent step. The guiding-in means 34 and the guiding-out means 35 are located close to the peripheral surface of the rotary drum 31 as shown in FIG. 1. The nonwoven fabric 10 is transported by nip rollers (not shown) provided upstream of the guiding-in means 34 and nip rollers (not shown) provided downstream of the guiding-out means 35. The downstream nip rollers are preferably configured to hold the nonwoven fabric by its edges or located at a position where the nonwoven fabric once having a temperature elevated by the hot air cools down near to room temperature so that the increased bulk may not decrease.

With the hot air generator and the evacuating means 32 in operation, the nonwoven fabric 10 unrolled from the stock roll 10' is fed to the peripheral surface of the rotary drum 31 by the guiding-in means 34 and transported a prescribed distance by the rotation of the rotary drum 31. During the transportation, more specifically while the nonwoven fabric 10 is moving around the space 31H (the region where hot air is sucked in), the hot air from the air supply duct 2 passes through the thickness of the nonwoven fabric 10 to accomplish hot air treatment on the nonwoven fabric 10.

The rotary drum 31 has a cylindrical peripheral surface. The peripheral surface around the entire circumference is formed of an air permeable material, such as a wire mesh or a punching metal sheet. The periphery of the rotary drum 31 inclusive of its peripheral surface is rotatably driven in the direction indicated by arrow A by an unshown driving source, such as a motor. The evacuating means 32 has a suction pipe one end of which is open to the inside of the rotary drum 31 and the other end of which is connected to an evacuator. On operating the evacuator, the evacuating means 32 is configured to evacuate part of the space inside the rotary drum 31, specifically a space 31H partitioned inside the drum and facing to the outlet 22 of the air supply duct 2 with the peripheral surface of the drum therebetween. The evacuator can be any of various known devices, such as a suction fan, a suction blower, and a vacuum pump.

With the evacuating means 32 in operation, the rotary sucking unit 30 operates to suck the hot air in the air supply duct 2 through the peripheral surface of the rotary drum 31 toward the space 31H, whereby the hot air is passed through the nonwoven fabric and sucked in the space 31H. The hot air taken into the evacuator 32 and thus recovered is returned to the hot air generator via a hot air return means (not shown). The return means includes a pipe connecting the evacuator 32 and the hot air generator and, if necessary, a blower fitted to the connecting pipe.

In the present embodiment, the housing 23 is provided with a cover 40 extending from near the lower end of the housing 23 toward the rotary sucking unit 30 so as to cover the nonwoven fabric 10. The cover 40 protects the peripheral surface of the rotary drum 31 over a region broader than the space 31H to prevent hot air from escaping. In order to sufficiently apply hot air to the nonwoven fabric, the angle $\theta$ formed by the space 31H inside the rotary drum 31 is preferably 90° to 320°, more preferably 180° to 300°. In the particular case shown in FIG. 1, the angle $\theta$ is 270°.

As shown in FIG. 2, the inlet 21 of the air supply duct 2 is open to the transverse direction of the nonwoven fabric 10 (direction X). The outlet 22 of the air supply duct 2 is open to the direction to face the peripheral surface of the rotary drum 31 and the nonwoven fabric 10.

The air supply duct 2 has an inflow portion 24 that leads the hot air from the inlet 21 to flow in parallel to the transverse direction (direction X) of the nonwoven fabric 10 and a outflow portion 25 that forms an angle with the inflow portion 24 to lead the hot air having flowed through the inflow portion 24 to the outlet 22. That is, the housing 23 constructing the air supply duct 2 is sectioned into the inflow portion 24 and the outflow portion 25. The outflow portion 25 causes the hot air having flowed in the inflow portion 24 to flow in a direction parallel to the thickness direction of the nonwoven fabric 10 (direction Z) to the outlet 22. The outflow portion 25 is preferably perpendicular to the inflow portion 24 as shown in FIG. 2.

The air supply duct 2 in the present embodiment has a horizontal tubular portion 2A extending horizontally and a vertical tubular portion 2B connected to the lower side of the horizontal tubular portion 2A at right angles. The horizontal tubular portion 2A forms the inflow portion 24, and the vertical tubular portion 2B forms the outflow portion 25. The horizontal tubular portion 2A mainly provides an inflow path 24A for hot air, and the vertical tubular portion 2B provides a plurality of outflow paths 25A for hot air. The horizontal tubular portion 2A has a cylindrical part at one end part thereof and the inlet 21 at the very end of the cylindrical part. The lower side of the other end part of the horizontal tubular portion 2A connects to the upper side of the vertical tubular portion 26B. Between the cylindrical part and the other end part having the vertical tubular portion 2B connected to the lower side thereof, the horizontal tubular portion 2A has a cross-sectionally rectangular part of which the upper and the lower face are parallel with each other. The lower face of that part and an extended plane of the lower face are indicated by a dashed-dotted line P1 in FIG. 2. In the inflow portion 24 above the line P1 there is a region 23c where the hot air flowing in the inflow path 24A strikes against the hereinafter described flow-facing part 26A of each of the hereinafter described baffle plates 26 to be diverted into a plurality of outflow paths 25A.

Figure 5:
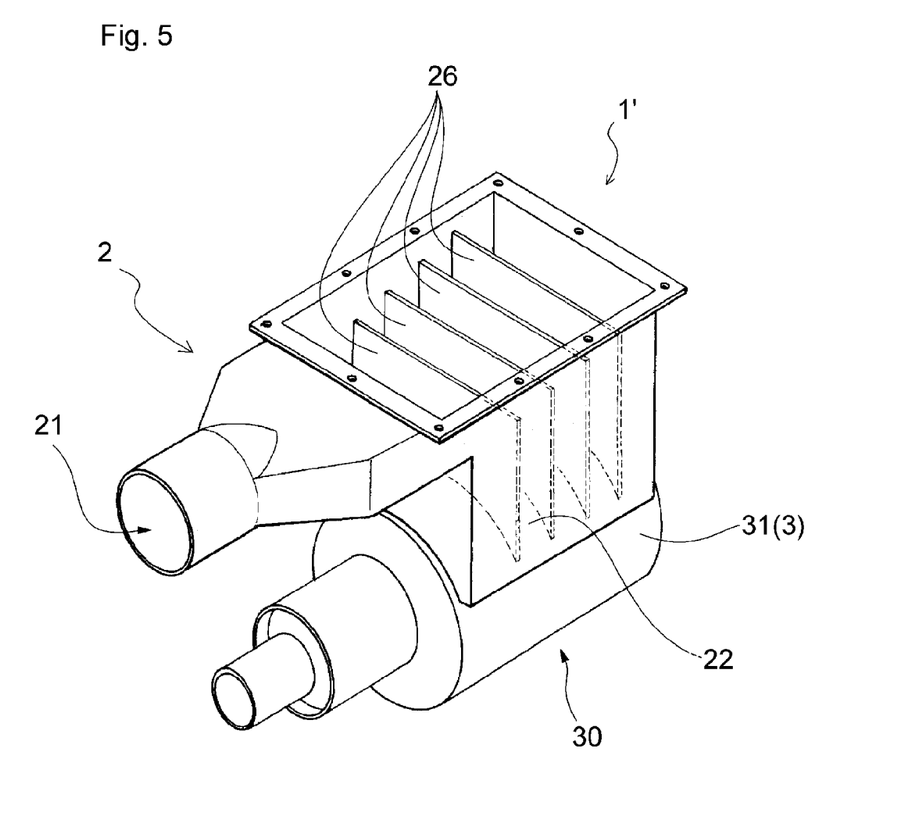
FIG. 5 is a perspective illustrating a part of an apparatus according to another embodiment of the invention.

As shown in FIG. 3, the housing 23 of the air supply duct 2 has a circular cross-section in its region 23a near the inlet 21 that admits hot air from the hot air generator so that it is easily connected via a hose or a like member to the hot air generator. In a region 23b of the housing 23 that forms the inflow portion 24, the cross-sectional shape gradually spreads laterally (in the direction Y in FIG. 3) up to a width equal to or larger than the diameter of the rotary drum 31. In the region 23c where the inflow path 24A is diverted to the outflow paths 25A, the housing 23 has outer walls 27 on four sides extending toward the rotary drum 31 to cover the upper peripheral part of the rotary drum 31. The topside of the housing 23 is closed by a top panel 28 that is removably fitted so as to allow adjusting the position of the hereinafter described baffle plates 26. FIGS. 3 and 5 show the housing 23 with the top panel 28 removed, while FIGS. 1 and 2 show the housing 23 with the top panel 28 attached.

As shown in FIG. 2, the air supply duct 2 has a plurality of baffle plates 26 each having a flow-facing part 26A and a flow-guiding part 26B located in the inflow portion 24 and the outflow portion 25, respectively. The flow-facing part 26A of the baffle plate 26 is located in the inflow portion 24 right across the direction of hot air flow (direction X) in the inflow path 24A. The flow-guiding part 26B of the baffle plate 26 is located in the outflow portion 25.

As shown in FIG. 2, the baffle plates 26 are arranged at different positions such that the inflow path 24A is stepwise narrowed. That is, the plurality of baffle plates 26 are arranged spacedly in the direction X such that, as shown in FIG. 2, the cross-sectional area of the inflow path 24A in the inflow portion 24 decreases progressively with distance from the inlet 21. The inflow path 24A is a passageway for gas flowing in the inflow portion 24 in the direction X. In the present embodiment, the distance t from the inflow path 24A to the upper end of the baffle plate 26 stepwise decreases with distance from the inlet 21. As a result, the cross-sectional area of the air passageway (inflow path) afforded above the upper end of the baffle plates 26 also decreases with distance from the inlet 21.

In the first embodiment, the height of the baffle plates 26 increases in equal increments in the hot air flow direction (direction X) thereby to stepwise reduce the cross-sectional area of the inflow path 24A so that equal amounts of the hot air flowing in the inflow portion 24 are successively struck against the baffle plates 26 to be diverted in flow direction and supplied to the respective outflow paths 25A. For the same purpose, the baffle plates 26 are disposed at equal intervals along the hot air flow direction.

The baffle plates 26 being disposed at different positions in the air supply duct 2 so as to stepwise narrow the inflow path 24A, every baffle plate 26 is divided into the flow-facing part 26A located in the inflow portion 24 to face and divert the hot air flow and the flow-guiding part 26B located in the outflow portion 25 to guide the hot air to the outlet in the thickness direction of the nonwoven fabric. The flow-guiding part 26B of every baffle plate 26 forms an outflow path 25A along with the outer wall 27 of the housing 23.

In the first embodiment, the air supply duct 2 is partitioned by a partition 24' parallel with the inflow path 24A into halves along the rotational direction of the rotary drum 31 as shown in FIG. 3. The partition 24' extends close to the top panel 28. In the first embodiment, one of the halves contains four baffle plates 26 arranged with their lower ends (the sucking part-side ends) even but the positions of their upper ends varied to progressively approach the top panel 28. The other half has the same structure with four baffle plates 26.

Each baffle plate 26 has straight edges along its upper end and both lateral sides and an arc-curved edge along its lower end (on the side of the sucking part 3) in conformity to the peripheral shape of the rotary drum 31. The baffle plate 26 is not particularly limited in material as long as it is capable of standing against hot air flowing in the inflow portion 24 and guiding the hot air toward the outlet 22. The baffle plate 26 is preferably made of an air impermeable material, such as stainless steel, aluminum or a like metal, a resin, paper, and so on.

The Z-directional position of each baffle plate 26 is changeable. That is, the length of its part located in the inflow portion 24, namely the length of the flow-facing part 26A is changeable. Each baffle plate may be formed of a single plate or a stack of a plurality of plates. In the latter case, the stacked plate is slid up and down to adjust the length of the flow-facing part 26A. Each baffle plate 26 may be configured to change its position in the direction X so as to change the interval between adjacent baffle plates 26.

The X-directional position and/or interval of the baffle plates 26 can be changed by, for example, slidably disposing each baffle plate upon two grooved bars spanning the vertical tubular portion 2B and fixing the baffle plates at respectively prescribed positions by nuts, or disposing a number of small plates in the vertical tubular portion 2B and fixing the baffle plates to these plates at respectively chosen positions.

To secure the flow-diverting effect of the baffle plates 26, it is preferred for each baffle plate 26 to be longer in the direction Z in its flow-guiding part 26B (the part extending from the flow-facing part 26A toward the outlet 22) than in the flow-facing part 26A located in the inflow portion 24. Specifically, the outflow portion 25 of the housing 23 of the air supply duct 2 preferably has a larger length (height H2) than the length (height H1) of the inflow portion 24 in the direction Z. When H1 is, e.g., 10 cm, the length L4 (see FIG. 2) of the flow-guiding part is preferably at least 15 cm, more preferably 20 to 30 cm, even more preferably 25 to 30 cm. From the standpoint of flow-diverting effect, the ratio of L4 to H2 is preferably at least 50%, more preferably 60% to 95%, even more preferably 70% to 90%.

The method for bulking nonwoven fabric using the above described bulking apparatus 1 will then be described. As shown in FIG. 1, the method according to a first embodiment includes performing hot air treatment on the nonwoven fabric 10 unrolled from the stock roll 10', i.e., the nonwoven fabric 10 wound in roll form. By this hot air treatment, the nonwoven fabric 10 having reduced its bulk due to the winding pressure increases (or recovers) the bulk to become bulky nonwoven fabric 10T. The stock rock 10' is located upstream of the bulking apparatus 1 in the direction of the travel of the nonwoven fabric 10. The nonwoven fabric 10 unrolled from the stock roll 10' by any known mechanism is transported by any known conveying mechanism, such as a set of feed rollers or a conveyor belt, to the bulking apparatus 1.

In the bulking apparatus 1, the introduced nonwoven fabric 10 is transported as held onto the peripheral surface of the rotary drum 31 by suction from the inside of the rotary drum 31. Hot air is fed from the outlet 22 of the air supply duct 2 open to the peripheral surface of the rotary drum 31 and blown through the nonwoven fabric 10 being transported, whereby the nonwoven fabric 10 increases in bulk.

As shown in FIG. 2, the hot air from the unshown hot air generator is admitted into air supply duct 2 through the inlet 21 and flows in the inflow path 24A extending parallel to the transverse direction of the nonwoven fabric 10 (direction X). Part of the flowing hot air strikes against the flow-facing part 26A of the baffle plates 26 disposed at intervals in the direction X and is thus diverted to the thickness direction of the nonwoven fabric 10 (direction Z). The diverted hot air flow is guided through the outflow paths 25A and blown from the outlet 22 to the nonwoven fabric 10.

In detail, part of the hot air flowing along the inflow path 24A of the inflow portion 24 strikes against the flow-facing part 26A of each baffle plate 26 and is therefore diverted to the direction along the outflow path 25A, i.e., toward the rotary drum (direction Z). The rest of the hot air that is not baffled by the baffle plate 26 further flows in the inflow portion 24, and part of which strikes against the next baffle plate 26 and is similarly diverted to the direction along the outflow path 25A. The part of the hot air that is not struck against any baffle plates 26 to the last is stopped by the outer wall 27 of the housing 23 of the air supply duct 2 and then diverted into the outflow path 25A. In that way, because the inflow path 24A is stepwise narrowed by baffle plates 26, the hot air admitted through the inlet 21 into the air supply duct 2 is stepwise baffled by the baffle plates 26 and diverted into the respective outflow paths 25A extending in the direction along the baffle plates 26. Because the hot air is portionwise diverted to flow in the respective outflow paths 25A each time it strikes against the baffle plate 26, the flow of the hot air is branched into a plurality of flow paths 25A that are separated from each other by the plurality of baffle plates 26.

The hot air thus flows in separate flow paths 25A along the flow-guiding part 26B of the baffle plates 26 in the outflow portion 25. The hot air branched and allowed to flow along a plurality of flow paths is blown through the outlet 22 onto the nonwoven fabric 10 being transported on the peripheral surface of the rotary drum 31. The nonwoven fabric 10 shown in FIG. 2 is being transported toward a viewer of FIG. 2. In FIG. 1, the hot air from the air supply duct 2 passes through the thickness of the nonwoven fabric 10 to perform hot air treatment while the nonwoven fabric 10 is travelling around the space 31H (the region where the hot air is sucked in).

The hot air blown and passed through the nonwoven fabric 10 is sucked through the peripheral surface of the rotary drum 31 into the inside and returned to the unshown hot air generator through the evacuating means 32 by an unshown returning means. The returned hot air is adjusted to a predetermined temperature in the hot air generator and reused to be supplied to the air supply duct 2.

Figures 4A, 4B:
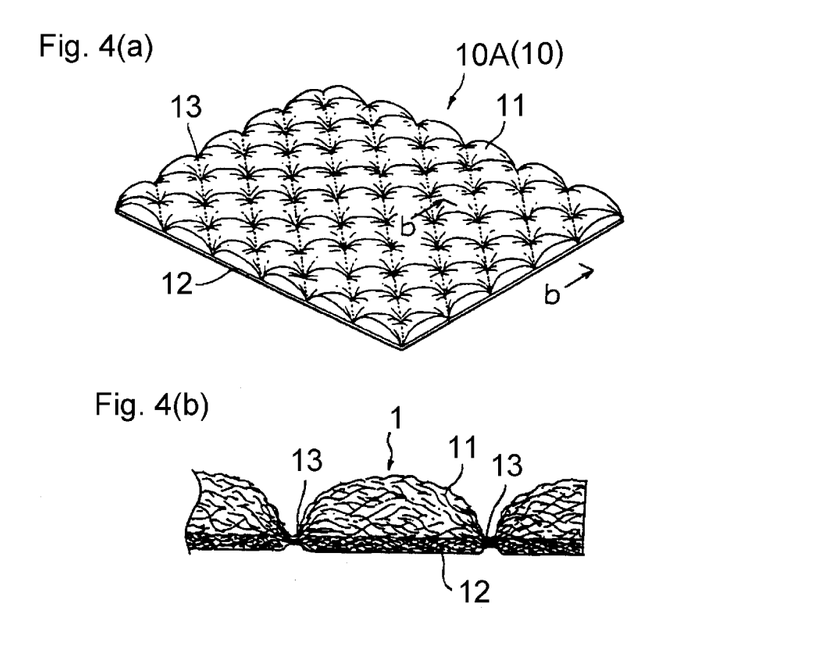
FIG. 4(a) is a perspective of an example of nonwoven fabric to be treated by the method of the invention.
FIG. 4(b) is a cross-section taken along line b-b in FIG. 4(a).

FIGS. 4(*a*) and 4(*b*) show a nonwoven fabric 10A, an example of the nonwoven fabric 10 to be allowed to increase (or recover) the bulk by the apparatus and/or method of the invention.

As is shown, the nonwoven fabric 10A has a three-dimensional bulky form with a dual-layer structure composed of a first layer 11 and an adjoining second layer 12. The first layer 11 and the second layer 12 are bonded in parts at a large number of bonds 13. The bonds 13 are arranged in a rhombic lattice pattern. The bonds 13 are compressed and densified portions, having a smaller thickness and a higher density than other portions of the nonwoven fabric 10A.

The nonwoven fabric 10A has a great number of closed regions surrounded by the bonds 13 arranged in a rhombic lattice pattern as described. In each of the closed regions, the first layer 11 forms a three-dimensional dome-shaped projection, while the second layer 12 is almost flat. As a whole, the nonwoven fabric 10A has a flat surface on the side of the second layer 12 and a great number of projections on the side of the first layer 11.

The first layer 11 contains thermoplastic fibers having crimps (hereinafter simply referred to as crimped fibers). Examples of crimped fibers include mechanically crimped fibers having a two-dimensional zig-zag crimp and fibers having a three-dimensional helical crimp. The first layer 11 may be made solely of crimped fibers or may contain heat bondable fibers, such as sheath/core conjugate fibers or side-by-side conjugate fibers, in addition to the crimped fibers. It is preferred for the fibers making up the first layer 11 have substantially no heat shrinkability or not shrink at a temperature at or below the heat shrinking temperature of the herein-after described heat shrinkable fibers contained in the second layer 12. On the other hand, the second layer 12 contains heat shrinkable fibers. The heat shrinkable fibers contained in the second layer 12 are preferably those having been three-dimensionally crimped into a helical configuration upon heat shrinkage.

Apparatus for Bulking Nonwoven Fabric

The method for preparing the nonwoven fabric 10A and the constituent fibers and other details of the nonwoven fabric 10A are described in commonly assigned patent application JP 2002-187228A. The method for preparation is described briefly as follows. A first carded web as a first layer is prepared using fiber materials containing crimped fibers. Separately, a second carded web as a second layer is prepared using fiber materials containing heat shrinkable fibers. The first carded web is laid on the second carded web, and the two webs are partly joined at bonds in a prescribed pattern by, for example, ultrasonic embossing. The resulting dual-layer structure is treated with hot air at a temperature at or above the heat shrinking temperature of the heat shrinkable fibers contained in the second carded web blown in a through-air system, whereby the second carded web is caused to thermally shrink, and the first carded web is caused to bulge in each of closed regions surrounded by the bonds to form a three-dimensional shape. At the same time, the constituent fibers are fusion bonded at their intersections to obtain the nonwoven fabric 10A. The thus obtained nonwoven fabric 10A is once wounded into roll form and stored.

The nonwoven fabric 10A decreases in bulk due to the winding pressure and the like. The present invention enables such nonwoven fabric 10A with decreased bulk to efficiently recover the loss of bulk.

One of the primary factors contributing to the increase (recovery) of bulk as a result of supplying hot air to the nonwoven fabric 10A is the recovery of bulk as a result of applying hot air to the crimped fibers present in the first layer 11. From this point of view, the temperature of the hot air blown to the nonwoven fabric 10A is preferably lower than the melting point (mp) of the crimped fibers and not lower than (mp−50)° C. To further ensure the bulk increasing (recovering) effect, the hot air temperature is more preferably from (mp−50)° C. to (mp−3)° C., even more preferably from (mp−30)° C. to (mp−5)° C.

Another factor contributory to the increase (recovery) of bulk as a result of supplying hot air is that the fibers, or intersections thereof, constituting the nonwoven fabric other than the crimped fibers are softened to become deformable. From this viewpoint, the temperature of the hot air blown to the nonwoven fabric 10A is particularly preferably from (mp−30)° C. to (mp−5)° C., wherein mp is the melting point of the thermoplastic fibers contained in the nonwoven fabric.

The nonwoven fabric to be bulked or rebulked by the invention is not limited to the one shown in FIGS. 4(*a*) and 4(*b*) and may be a single- or multi-layered structure containing crimped fibers or a single- or multi-layered structure containing crimped fibers and heat shrinkable fibers. For example, a three- or more-layered nonwoven fabric containing crimped fibers in one or both of its outermost layers and heat shrinkable fibers in an inner layer or layers between the outermost layers may be treated by the invention.

Nonwoven fabric containing no crimped fibers but containing fibers extensible on heating (hereinafter called "heat extensible fibers") is also useful.

The nonwoven fabric containing heat extensible fibers may be a single-layered structure obtained by making a web of heat extensible fibers, forming debossed portions in a lattice pattern by heat sealing, ultrasonic sealing, high frequency sealing or otherwise embossing, and subjecting the web to a hot air treatment, such as a through-air treatment or a hot air blow treatment, to cause the heat extensible fibers to extend. The nonwoven fabric containing heat extensible fibers may also be a laminate structure obtained by stacking a web of heat extensible fibers on a separately prepared fiber web or nonwoven fabric, and forming debossed portions in a lattice pattern, followed by performing a hot air treatment in the same manner as described above. The nonwoven fabric of the type described has projections formed on one or both sides thereof as a result of extension of the heat extensible fibers between the debossed portions and preferably has fusion bonds of fibers formed at intersections of heat extensible fibers in other than the debossed portions. The heat extensible fibers preferably extend at temperatures at or above 90° C., more preferably from 110° to 140° C. Examples of useful heat extensible fibers include those fibers made of a resin the crystal state of which changes on being heated to cause the fibers to stretch and crimped fibers the crimp of which is undone on being heated to let the fibers extend. In the case of multi-layered nonwoven fabric composed of a fiber layer containing heat extensible fibers and another fiber layer, the other fiber layer may be made solely of heat bondable fibers having no heat extensibility or may contain heat extensible fibers in a lower proportion than in the fiber layer containing heat extensible fibers. The heat extensible fibers may be conjugate fibers made of a first resin component having an orientation index of 20% to 80% (preferably 40% to 70%) and a second resin component having a lower melting or softening point than the melting point of the first resin component and an orientation index of 10% to 80% (preferably 20% to 60%), the second resin component being present to cover at least part of the fiber surface continuously in the longitudinal direction.

Nonwoven fabrics obtained by various processes may be used to be bulked as the nonwoven fabric 10. Any nonwoven fabric is bulkable by the invention with no particular limitation, including spun-bonded, hydroentangled, resin-bonded, and needle-punched nonwovens. Particularly preferred are air-through nonwovens obtained by a through-air system that is suited to produce bulky nonwoven fabric and to achieve high bulk recovery and increase. Air-through nonwoven fabric is obtained by consolidating a carded or airlaid fiber web by applying hot air in a through-air system. A nonwoven fabric laminated with a resin film is also bulkable by the invention.

The nonwoven fabric 10 to be bulked may be a nonwoven fabric composed of two layers laminated on each other to create a three-dimensional structure. Specifically, such a nonwoven fabric is obtained by bonding an upper nonwoven layer and a lower nonwoven layer at a large number of bonds. The upper nonwoven layer has a large number of hollow projections in regions other than the bonds. For use as, for example, a topsheet of a disposable diaper, the upper nonwoven layer provides the skin contact surface (the surface facing the wearer's skin), and the lower nonwoven layer defines the side facing an absorbent member. The projections and the depressions (bonds) are arranged alternately, faulting lines in both the X direction and the Y direction. Each of the upper and the lower nonwoven layer exhibits substantially no extensibility. Such a nonwoven laminate fabric having a three-dimensional structure is obtained by, for example, making a three-dimensionally textured nonwoven fabric by passing between intermeshing toothed rollers or otherwise relief-patterning, stacking the thus textured nonwoven fabric and another nonwoven fabric, and partly bonding the two nonwoven fabrics at the depressions or projections of the textured nonwoven fabric by heat fusion or a like means. Examples of such nonwovens having a three-dimensional structure include the sheets described in JP 2002-187228A, JP 2004-345357A, and JP 2004-275296A.

The invention is effective in not only recovering the loss of bulk of nonwoven fabrics caused by winding pressure and the like but also bulking (increasing the bulk of) originally thin nonwoven fabrics. For example, the invention is useful for the purpose of increasing the bulk of a nonwoven fabric containing heat extensible fibers by causing the heat extensible fibers to thermally extend as well as increasing or recovering the bulk of the above discussed nonwoven fabric containing heat shrinkable fibers.

The increased bulk being taken advantage of, the bulky nonwoven fabrics obtained using the bulking apparatus or method of the invention are useful in various applications, typically as a member making up absorbent articles, such as sanitary napkins and disposable diapers.

An absorbent article, such as a sanitary napkin or a disposable diaper, includes a liquid permeable topsheet, liquid impermeable backsheet, and a liquid retentive absorbent member interposed between the two sheets. An absorbent article additionally having a liquid permeable sublayer sheet between the topsheet and the absorbent member is also known. When used as a topsheet or sublayer sheet in an absorbent article, a bulky nonwoven fabric having the structure shown in FIGS. 4(a) and 4(b) will have reduced rewet and excellent downward fluid wicking properties with little lateral diffusion of fluid by virtue of its high bulkiness. Furthermore, such a topsheet or sublayer sheet will not cause a body fluid to remain thereon and exhibit good permeability to highly viscous fluids. Particularly because the above discussed nonwoven fabric has a three-dimensional structure and high bulk as shown in FIGS. 4(a) and 4(b), the recovered bulk will enable the nonwoven fabric to demonstrate its essential bulkiness both perceptually and visually.

The above described absorbent article is produced as follows. A nonwoven fabric 10 wound into a stock roll 10' is unrolled and introduced into the bulking apparatus 1, where it gains or recovers bulk before being assembled into an absorbent article. The nonwoven fabric 10 having been thus bulked by hot air treatment is subsequently sent to the absorbent article production line (not shown). That is, the nonwoven fabric 10 is introduced into a processing apparatus (not shown) for producing the absorbent article that is installed downstream from the bulking apparatus, where it is combined and united with other sheets and constituent materials and cut into individual absorbent articles.

In the case where the nonwoven fabric 10 having the thus increased (recovered) bulk is subsequently forwarded to a processing step as described above, it is preferably transported to the next processing step while being in the rebulked state, i.e., without being once wound up. While in a processing apparatus the nonwoven fabric 10 is often subjected to a processing step that can reduce the bulk of the nonwoven fabric 10, such as pressing between nip rollers, the nonwoven fabric 10 having once recovered the bulk by the above mentioned method is less likely to greatly decrease in bulk even when subjected to pressing or a like step.

By the use of the bulking apparatus and method according to the first embodiment, a precisely controlled amount of hot air at a precisely controlled temperature can be supplied from the air supply duct 2 to the nonwoven fabric 10 being transported, whereby the bulk of the nonwoven fabric is increased or recovered with good precision. Therefore, it is possible to easily and efficiently bulk or rebulk the nonwoven fabric 10 that has been under winding pressure or otherwise undergone reduction in bulk. In particular, to arrange the baffle plates 26 at a regular interval and with a constant increment in height of their flow-facing part 26A allows for uniformly controlling the temperature and the amount of hot air to be delivered through the outflow paths 25A in the outflow portion 25 to the nonwoven fabric 10, thereby to accomplish uniform increase (recovery) in bulk in the transverse direction of the nonwoven fabric 10 (direction X).

The method for making an absorbent article according to the invention, which uses a nonwoven fabric having been bulked with good precision, can stably produce an absorbent article providing various high performance properties required of an absorbent article.

The apparatus of the first embodiment has the baffle plates 26 disposed in a configuration that provides a gradually narrowing inflow path 24A in the air supply duct 2. This configuration allows for compact design of the bulking apparatus that achieves bulking nonwoven fabrics while precisely controlling the temperature and the amount of hot air to be supplied.

Since the apparatus of the first embodiment has the inlet 21 open to the transverse direction of the nonwoven fabric 10 being transferred (direction X) in the air supply duct 2, it is space-saving and easy to install, i.e., has high installability, to an existing production step, such as a step of conveying a nonwoven fabric or a step for making an absorbent article.

The apparatus and method of the first embodiment use a rotary drum 31 of a rotary sucking unit as a sucking part, around which the nonwoven fabric 10 is wrapped and transported by suction, and hot air is supplied to the so moving nonwoven fabric. This design allows hot air to be supplied over a large area of the nonwoven fabric and yet makes the apparatus compact thereby providing an efficient apparatus and method. Additionally, the design makes it possible to directly rotate the axis of the rotary drum using a servo motor or other rotating means so that the nonwoven fabric may be transported while being treated to increase its bulk in a stable manner even at a high rotation speed.

The apparatus and method for bulking nonwoven fabric according to the invention are not at all limited to the aforementioned embodiments, and various changes and modifications can be added thereto as follows.

While in the first embodiment the baffle plates 26 are arranged at a regular interval and with a constant increment in height, the interval and/or the change of height may be varied according to the necessity. For example, the length of the flow-facing part 26A and/or the distance between adjacent baffle plates 26 may be increased in a region corresponding to a transversely (X-directionally) middle portion of the nonwoven fabric 10 so as to supply an increased amount of hot air thereby to increase (or recover) the bulk of that portion of the nonwoven fabric more than the rest. Similarly, the amount of hot air flowing in a region corresponding to both side portions (opposite in the direction X) of the nonwoven fabric 10 may be increased to increase (or recover) the bulk of that portion of the nonwoven fabric more than the rest or to prevent the nonwoven fabric from fluttering.

The number of the baffle plates arranged in the air supply duct 2 spacedly in the direction X may be changed from four to two or three or more than four. For example, in the case when a 100 cm wide web of nonwoven fabric is to be bulked, the number of baffle plates to be disposed is preferably 5 to 30, more preferably 8 to 20.

The rotary drum 31 as a sucking part 3 may be replaced with a suction box mounted above an air permeable belt conveyor. In this case, it is desirable to shape the outlet side of the air supply duct to the shape of the belt conveyor.

The partition partitioning the air supply duct 2 in the rotating direction of the rotary drum 31 shown in FIG. 3 may be dispensed with. In that case, the inflow portion 24 and the outflow portion 25 are defined and partitioned by the baffle plates 26 and the housing 23 as in the bulking apparatus 1' shown in FIG. 5.

Figure 6:
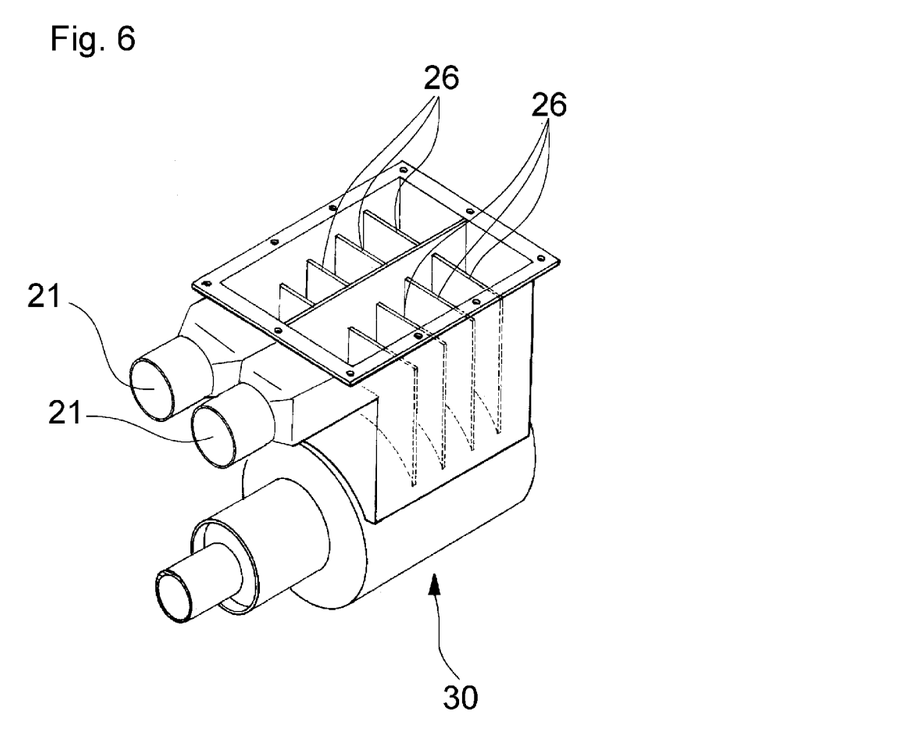
FIG. 6 is a perspective illustrating a part of a bulking apparatus according to still another embodiment of the invention.

The horizontal tubular portion 2A of the air supply duct 2 may have two horizontal tubular portions extending toward the outer wall 27 closest to the inlet 21 and having the respective outlets 21 as shown in FIG. 6. This configuration allows for supplying two flows of hot air different in temperature and/or flow speed from their respective inlets 21.

Figure 7:
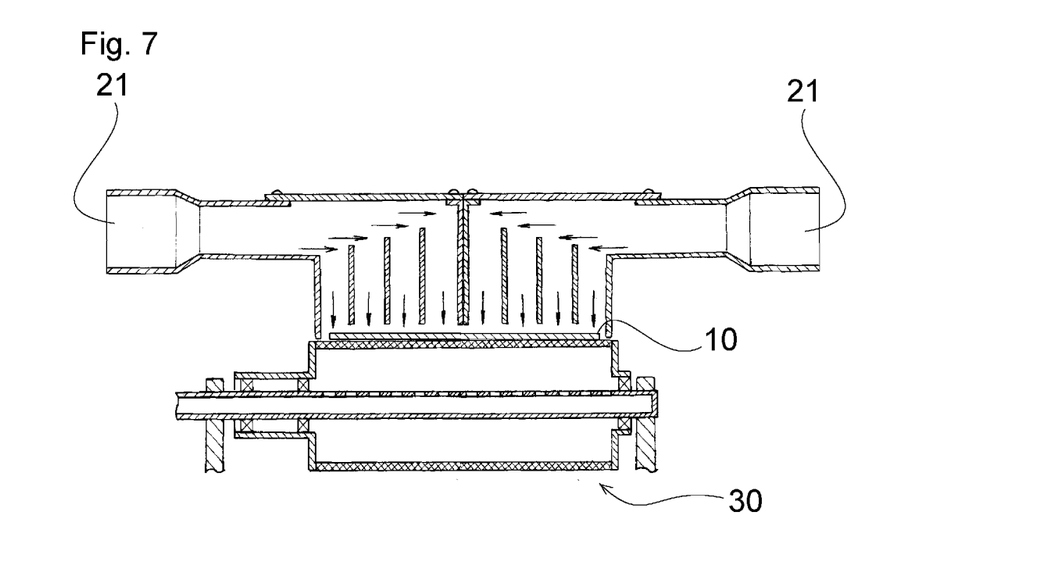
FIG. 7 is a schematic cross-section of a bulking apparatus according to yet another embodiment of the invention.

The bulking apparatus may have two air supply ducts 2 arranged in the transverse direction of the nonwoven fabric and having the respective inlets 21 on the opposite sides as shown in FIG. 7. This configuration is effective in treating nonwoven fabric with a large width.

EXAMPLES

The invention will now be illustrated in greater detail with reference to Examples, it being understood that the invention is not limited thereto.

Example 1

A bulking apparatus shown in FIGS. 1 through 3 was made. The dimensions indicated in FIGS. 2 and 3 were as follows: L1=55 cm; L2=20 cm; L3=22 cm; H1=55 mm; and H2=80 mm.

Four baffle plates made of stainless steel were disposed in each of the partitioned regions of the air supply duct 2 at an interval of 40 mm along the direction of the inflow path 24A. The height of the four baffle plates was increased by an increment of 11 mm within the height H1 (55 mm) of the inflow portion 24. The least length L4 (see FIG. 2) of the flow-guiding part 26B was 60 mm. Each baffle plate was formed of two plates, one of which was vertically slidable to provide different heights of the flow-facing part 26A. The air supply duct 2 was mounded on the rotary drum 31 equipped with the evacuating means 32, and the air supply duct 2 thus combined with the rotary drum 31 was connected to a hot air generator.

Comparative Examples 1 and 2

A bulking apparatus of Comparative Example 1 was constructed in the same manner as in Example 1, except that the baffle plates were removed from the air supply duct 2 of Example 1, and the resulting air supply duct was mounted on the rotary drum 31.

A bulking apparatus of Comparative Example 2 was constructed in the same manner as in Example 1, except for replacing the baffle plates used in Example 1 with the corresponding flow-facing part 26A of the baffle plates of Example 1.

Evaluation

Hot air of 110° C. was supplied to each bulking apparatus, and the temperature and flow speed of the hot air were measured at positions 5 mm above the highest position of the peripheral surface of the rotary drum in each of the outflow paths 25A. The measuring positions were designated A to E in the order of distance from the inlet 21. In Comparative Examples 1 and 2, in which there were no baffle plates at the measuring positions, measurements were taken at the same positions as A to E. The results obtained are shown in Table 1 below.

TABLE 1

| Measuring Position | Parameter to be Measured | Example 1 | Compara. Example 1 | Compara. Example 2 |
|---|---|---|---|---|
| A | Temp. (° C.) | 105 | 85 | 80 |
|   | Flow Speed (m/sec) | 4.4 | 1.6 | 2.6 |
| B | Temp. (° C.) | 108 | 91 | 96 |
|   | Flow Speed (m/sec) | 4.4 | 3.7 | 4.4 |
| C | Temp. (° C.) | 108 | 99 | 105 |
|   | Flow Speed (m/sec) | 4.0 | 3.6 | 5.4 |
| D | Temp. (° C.) | 107 | 107 | 109 |
|   | Flow Speed (m/sec) | 4.7 | 6.3 | 3.9 |
| E | Temp. (° C.) | 105 | 108 | 107 |
|   | Flow Speed (m/sec) | 5.1 | 7.2 | 1.7 |

The temperatures and flow speeds measured at positions A to E were almost constant in Example 1. In Comparative Example 1 using no baffle plates 26, the flow speed and the temperature both increased with distance from the inlet 21. In Comparative Example 2 using baffle plates having no flow-guiding part 26B, the temperature and the flow speed were high at position C and low at positions A and E, revealing that the flow-facing parts 26A were able to evenly change the flow of the hot air but failed to exert the flow diverting effect up to the vicinities of the rotary drum 31.

INDUSTRIAL APPLICABILITY

By the use of the apparatus and method for bulking nonwoven fabric according to the invention, the bulk of nonwoven fabric can be increased by treatment with a precisely controlled amount of hot air at a precisely controlled temperature using compact equipment.

According to the method for making an absorbent article of the invention, because of use of nonwoven fabric having a precisely increased bulk, an absorbent article providing various high performance properties required of an absorbent article can be produced in a stable manner.

The invention claimed is:

1. An apparatus for bulking nonwoven fabric comprising a hot air generator, an air supply duct having an inlet for receiving hot air from the hot air generator and an outlet for delivering the hot air to nonwoven fabric being transported, and a sucking part sucking in hot air delivered from the outlet to the nonwoven fabric and passed through the nonwoven fabric,
the air supply duct having an inflow portion providing an inflow path and an outflow portion, the inflow portion leading the hot air introduced into the inlet to flow in parallel to the transverse direction of the nonwoven fabric, and the outflow portion forming an angle with the inflow portion to lead the hot air having flowed through the inflow portion to the outlet,
the air supply duct having a plurality of baffle plates disposed therein, each baffle plate having a flow-facing part and a flow-guiding part located in the inflow portion and the outflow portion, respectively, the plurality of baffle plates being arranged such that the inflow path in the inflow portion has a decreasing cross-sectional area with distance from the inlet,
wherein each baffle plate is longer in its flow-guiding part than in its flow-facing part.

2. The apparatus for bulking nonwoven fabric according to claim 1, wherein the sucking part is a rotary drum of a rotary sucking unit.

3. The apparatus for bulking nonwoven fabric according to claim 1, wherein the sucking part has a means for returning the sucked hot air to the hot air generator.

4. The apparatus for bulking nonwoven fabric according to claim 1, wherein each baffle plate has a changeable length in its part located in the inflow portion.

5. The apparatus for bulking nonwoven fabric according to claim 1, wherein the air supply duct is partitioned by a partition parallel to the inflow path.

6. The apparatus for bulking nonwoven fabric according to claim 1, wherein the inlet comprises two inlets.

7. The apparatus for bulking nonwoven fabric according to claim 1, wherein the air supply duct comprises two air supply ducts arranged in the transverse direction of the nonwoven fabric, the air supply ducts having the respective inlets open to the opposite directions.

8. The apparatus for bulking nonwoven fabric according to claim 1, wherein the ratio of length of the flow-guiding part of the baffle plate to height of the outflow portion of the air supply duct is 60% to 95%.

9. The apparatus for bulking nonwoven fabric according to claim 1, wherein the sucking part is a rotary drum of a rotary sucking unit, and
the baffle plate has straight edges along its upper end and both lateral sides and an arc-curved edge on the side of the sucking part in conformity to the peripheral shape of the rotary drum.

10. The apparatus for bulking nonwoven fabric according to claim 2, wherein the rotary sucking unit comprises a rotary drum as the sucking part that has an air permeable peripheral surface, an evacuating means that evacuates the inside of the rotary drum, a guiding-in means that guides the nonwoven fabric from a prescribed position of the bulking apparatus onto the peripheral surface of the rotary drum, and a guiding-out means that separates the nonwoven fabric having been transported over a prescribed distance as wrapped around the peripheral surface of the rotary drum from the peripheral surface of the rotary drum and delivers the separated nonwoven fabric to a subsequent step.

11. A method for bulking nonwoven fabric being transported by suction using hot air supplied from the outlet of an air supply duct and passed through the nonwoven fabric,
the method comprising introducing hot air generated in a hot air generator into an air supply duct through an inlet, advancing the hot air in the air supply duct in a direction parallel to the transverse direction of the nonwoven fabric, directing the hot air against a plurality of baffle plates arranged spacedly in the direction parallel to the transverse direction of the nonwoven fabric such that the flow of the hot air is diverted to the thickness direction of the nonwoven fabric while being branched into a plurality of paths separated from each other by the baffle plates, and delivering the hot air having flowed through the plurality of paths to the nonwoven fabric,
further comprising bulking nonwoven fabric with the apparatus for bulking nonwoven fabric according to claim 1.

12. The method for bulking nonwoven fabric according to claim 11, wherein the hot air branched into the flow paths flows along the flow-guiding part of the baffle plate in the outflow portion.

13. A method for making an absorbent article using a nonwoven fabric obtained by the method for bulking nonwoven fabric according to claim 11,
the method comprising superposing the nonwoven fabric on a sheet material, uniting the nonwoven fabric and the sheet material, and cutting the united nonwoven fabric and the sheet material into an individual absorbent article.

\* \* \* \* \*